United States Patent [19]

Böckmann et al.

[11] 4,294,777

[45] Oct. 13, 1981

[54] COLOR-STABILIZED AROMATIC CARBOXYLIC ACID CHLORIDES AND A PROCESS FOR THEIR PREPARATION

[75] Inventors: Walter Böckmann; Karl-August Lipper; Friedrich Brühne, all of Krefeld, Fed. Rep. of Germany

[73] Assignee: Bayer Aktiengesellschaft, Leverkusen, Fed. Rep. of Germany

[21] Appl. No.: 85,553

[22] Filed: Oct. 17, 1979

[30] Foreign Application Priority Data

Nov. 8, 1978 [DE] Fed. Rep. of Germany ....... 2848356

[51] Int. Cl.³ .............................................. C07C 51/64
[52] U.S. Cl. ................................................. 260/544 D
[58] Field of Search .............. 260/544 D; 252/400 A, 252/405, 407

[56] References Cited

U.S. PATENT DOCUMENTS

| 3,349,123 | 10/1967 | Flaxman | 252/400 A |
| 3,520,809 | 7/1970 | Spaaks | 252/407 |
| 3,923,912 | 12/1975 | Beckers | 252/407 |

OTHER PUBLICATIONS

Nass, Chem. Abst., vol. 74, #32211p (1971).

*Primary Examiner*—Robert Gerstl
*Assistant Examiner*—James H. Reamer
*Attorney, Agent, or Firm*—Sprung, Felfe, Horn, Lynch & Kramer

[57] ABSTRACT

A process for color stabilizing aromatic carboxylic acid chloride against discoloration which comprises introducing into a composition containing an aromatic carboxylic acid chloride 0.001 to 2% by weight of a color stabilizer, based upon the amount of said aromatic carboxylic acid chloride. The use of aldehydes, ketones, olefins, phosphorus and arsenic containing compounds are contemplated as stabilizer.

15 Claims, No Drawings

COLOR-STABILIZED AROMATIC CARBOXYLIC ACID CHLORIDES AND A PROCESS FOR THEIR PREPARATION

The invention relates to color-stabilized aromatic carboxylic acid chlorides and a process for their preparation.

Aromatic carboxylic acid chlorides which can be obtained, for example, by reacting the corresponding aromatic carboxylic acids with benzotrichloride frequently have the unpleasant property of becoming discolored on storage. Discoloration of the aromatic carboxylic acid chlorides can even still occur after distillation thereof.

It it is important for the further reaction of the aromatic carboxylic acid chlorides that they are colorless, prior distillation is necessary.

While the chemical formula and precise components of the impurities are unknown, it is believed that free chlorine gives to the aromatic carboxylic acid chlorides a yellow coloration, while free bromine imparts a brown coloration.

It has now been found that the discoloration of the aromatic carboxylic acid chlorides can be avoided by adding a stabilizer in an amount of 0.001 to 2% by weight, relative to the aromatic carboxylic acid chlorides.

A particular advantage of color stabilization, according to the invention, of aromatic carboxylic acid chlorides is that on the one hand the stabilization is permanent and on the other hand the color-stabilized aromatic carboxylic acid chlorides can, surprisingly, be used for further reactions, for example Friedel-Crafts acylation reactions, without problems, that is to say without impairment of the reactivity of the aromatic carboxylic acid chlorides.

Examples of aromatic carboxylic acid chlorides which can be color-stabilized by the process according to the invention are those of the general formula (I)

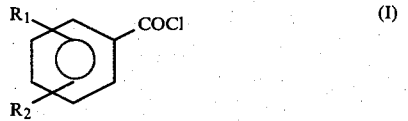

wherein
$R_1$ and $R_2$ can be identical or different and represent hydrogen, halogen or optionally substituted alkyl or alkoxy radicals.

Examples of contemplated optionally substituted alkyl or alkoxy radicals are those with up to 10 C atoms, preferably up to 4 C atoms, for example alkyl radicals such as methyl, ethyl, n-propyl, iso-propyl, n-butyl, iso-butyl, tert.-butyl, n-pentyl, iso-pentyl, 2-methylpentyl, 3-methylpentyl, n-hexyl, n-heptyl, n-octyl, iso-octyl, n-nonyl, n-decyl and cyclohexyl, preferably methyl, ethyl, n-propyl, iso-propyl, n-butyl, iso-butyl and tert.-butyl; and alkoxy radicals such as methoxy, ethoxy, propoxy, butoxy, pentyloxy and hexyloxy, preferably methoxy and ethoxy.

Halogens which may be mentioned are fluorine, chlorine and bromine, preferably chlorine.

The following aromatic carboxylic acid chlorides, for example, are preferably color-stabilized: benzoyl chloride, o-toluic acid chloride, p-toluic acid chloride, 2-chloro-benzoyl chloride, 3-chloro-benzoyl chloride, 4-chloro-benzoyl chloride, 2,4-dichlorobenzoyl chloride and anisic acid chloride.

Color stabilizers which are used for the process according to the invention are, for example, those of the general formula (II)

wherein
$R_3$ and $R_4$ can be identical or different and represent hydrogen, halogen, hydroxy or optionally substituted alkoxy, aryloxy, aralkoxy, alkyl, aralkyl, aryl, alkenyl or mono- or di-alkylamino radicals, and $R_3$ and $R_4$, with the carbonyl group, can furthermore form an optionally substituted ring. Halogens which may be mentioned are fluorine, chlorine and bromine, preferably chlorine.

Examples of possible radicals $R_3$ and $R_4$ in the above mentioned formula are hydrocarbon radicals with up to 12 C atoms, preferably up to 8 C atoms, for example alkoxy radicals, such as methoxy, ethoxy, propoxy, butoxy, tert.-butoxy, pentyloxy and hexyloxy, preferably methoxy and ethoxy; aryloxy radicals, such as phenoxy, chlorophenoxy and methylphenoxy, preferably phenoxy; aralkoxy radicals, such as benzyloxy, p-chlorobenzyloxy and p-methylbenzyloxy, preferably benzyloxy; alkyl radicals, such as methyl, ethyl, n-propyl, iso-propyl, n-butyl, iso-butyl, tert.-butyl, n-pentyl, iso-pentyl, 2-methylpentyl, 3-methylpentyl, n-hexyl, n-octyl, iso-octyl, n-nonyl, n-decyl and n-dodecyl, preferably methyl, ethyl, n-propyl and iso-propyl; aralkyl radicals, such as benzyl, p-chloro-benzyl and p-methylbenzyl, preferably benzyl; aryl radicals, such as phenyl, toluyl, p-chlorophenyl and p-methoxyphenyl, preferably phenyl and toluyl; alkenyl radicals, such as vinyl, propenyl, allyl, buten-1-yl, buten-2-yl and methallyl, preferably vinyl, propenyl and methallyl; mono- and di-alkylamino radicals, such as methylamino, ethylamino, propylamino, dimethylamino, diethylamino and dipropylamino, preferably dimethylamino and diethylamino; and alkylene radicals, in which one or more methylene groups can optionally be replaced by hetero-atoms, such as ethylene, trimethylene, tetramethylene, pentamethylene, hexamethylene, 2-oxatrimethylene, 1-thiatrimethylene and 1-iminopentamethylene, preferably pentamethylene and 1-iminopentamethylene.

Color stabilizers which are used for the process according to the invention are furthermore those of the general formula (III)

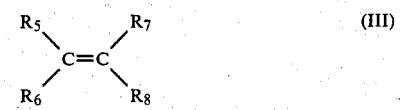

wherein
$R_5$ to $R_8$ can be identical or different and represent hydrogen, nitrile, halogen, carboxyl or optionally substituted carbalkoxy, carbaryloxy, alkoxy, aryloxy, acyloxy, alkyl, aryl, aralkyl or alkenyl radicals, and $R_5$ and $R_6$, and/or $R_7$ and $R_8$, or $R_5$ and $R_7$, and/or $R_6$ and $R_8$, with the atoms to which they are linked, can furthermore form an optionally substituted ring.

Halogens which may be mentioned are fluorine, chlorine and bromine, preferably chlorine.

Examples of contemplated radicals $R_5$ to $R_8$ in the above-mentioned formula are hydrocarbon radicals with up to 12 C-atoms, preferably up to 8 C-atoms, for example carbalkoxy radicals, such as carbomethoxy, carboethoxy, carbopropoxy, carbobutoxy, carbo-tert.-butoxy, carbopentyloxy, cabohexyloxy, preferably carbomethoxy and carboethoxy; carboaryloxy radicals, such as carbophenoxy, carbomethylphenoxy, carbochlorophenoxy, preferably carbophenoxy; alkoxy radicals, such as methoxy, ethoxy, propoxy, butoxy, tert.-butoxy, pentyloxy and hexyloxy, preferably methoxy and ethoxy; aryloxy radicals, such as phenoxy, chlorophenoxy and methylphenoxy, preferably phenoxy; acyloxy radicals, such as acetoxy, propionyloxy, butyryloxy, benzoyloxy and chlorobenzoyloxy, preferably acetoxy and benzoyloxy; alkyl radicals, such as methyl, ethyl, n-propyl, iso-propyl, n-butyl, iso-butyl, tert.-butyl, n-hexyl, n-octyl, n-nonyl and dodecyl, preferably methyl, ethyl, n-propyl and iso-propyl; aralkyl radicals, such as benzyl, p-chlorobenzyl and p-methylbenzyl, preferably benzyl; aryl radicals, such as phenyl, toluyl, p-chlorophenyl and p-methoxyphenyl, preferably phenyl and toluyl; alkenyl radicals, such as vinyl, propenyl, allyl, buten-1-yl, buten-2-yl and methallyl, preferably vinyl, allyl and methallyl; and alkylene radicals, in which one or more methylene groups can optionally be replaced by hetero-atoms, such as ethylene, trimethylene, tetramethylene, pentamethylene, hexamethylene, 2-oxatrimethylene and 1-thiatrimethylene, preferably tetramethylene and pentamethylene.

Color stabilizers which can be used for the process according to the invention are furthermore those of the general formula (IV)

(IV)

wherein $R_9$ to $R_{11}$ can be identical or different and represent halogen or optionally substituted alkyl, aryl, alkoxy or aralkoxy radicals and X denotes phosphorus or arsenic.

Examples of contemplated optionally substituted alkyl, aryl, alkoxy or aralkoxy radicals are those with up to 12 C atoms, preferably up to 8 C atoms, for example alkyl radicals such as methyl, ethyl, n-propyl, iso-propyl, n-butyl, iso-butyl, tert.-butyl, n-hexyl, n-octyl, n-nonyl, n-decyl and n-dodecyl, preferably methyl, ethyl, n-propyl and isopropyl; alkoxy radicals such as methoxy, ethoxy, propoxy, butoxy, pentyloxy snd hexyloxy, preferably methoxy and ethoxy; aralkoxy radicals such as benzyloxy, p-chlorobenzyloxy and p-methylbenzyloxy, preferably benzyloxy; and aryl radicals such as phenyl, toluyl, p-chlorophenyl and p-methoxyphenyl, preferably phenyl and toluyl.

Halogens which may be mentioned are: fluorine, chlorine and bromine, preferably chlorine and bromine.

Preferred color stabilizers which are used for the aromatic carboxylic acid chlorides are: acetone, methyl ethyl ketone, diethyl ketone, benzaldehyde, acetophenone, ethyl acetoacetate, acrylic acid ethyl ester, methacrylic acid methyl ester, crotonic acid, vinyl acetate, maleic acid, maleic acid diethyl ester, fumaric acid diethyl ester, dicyclopentadiene, $\epsilon$-caprolactam, styrene, methyl vinyl ketone, acrolein, cyclohexene, allyl chloride, cinnamic acid, allyl alcohol, acetaldehyde, triethyl phosphite, triphenylphosphine, phosphorus trichloride, arsenic trichloride, methacrylic acid amide and cyclohexanone, acetone, cyclohexanone, dicyclopentadiene, ethyl acetoacetate, maleic acid, $\epsilon$-caprolactam, triethyl phosphite and phosphorus trichloride being particularly preferred.

$\epsilon$-Caprolactam is very particularly preferably employed in the process according to the invention.

The compounds mentioned, of the general formula (II), (III) and (IV), can be used individually or as mixtures with one another for color-stabilization of the aromatic carboxylic acid chlorides of the general formula (I), the mixing ratio being of no importance with regard to the activity of the stabilizers.

The amount of compounds of the general formula (II), (III) and (IV) used as color stabilizers which is added to the aromatic carboxylic acid chlorides is preferably 0.01 to 0.5% by weight, and in particular 0.02 to 0.1% by weight.

One can also add the compounds of the general formula (II), (III) and (IV), used as color stabilizers, as a solution in an inert solvent if this appears appropriate, for example for the purpose of easy metering or easier thorough mixing, but in general this is not necessary. Examples of suitable inert solvents are benzene, toluene, xylene, cyclohexane and carbon tetrachloride.

The concentration of the solution of color stabilizers in the solvent is appropriately chosen so that it is at the upper limit of the solubility of the color stabilizers in order to keep the resulting concentration of the solvent in the aromatic carboxylic acid chlorides as low as possible, for example a weight ratio of 50 to 50 is preferred for the toluene/phosphorus trichloride system.

The invention furthermore relates to the aromatic carboxylic acid chlorides, color-stabilized in the above manner, as such.

EXAMPLE 1

0.05 g of acetone is dissolved in 100 g of benzoyl chloride. The sample is stored in the dark. The mixture is still colorless after months. On the other hand, an untreated sample of the same material had a color number of 150 APHA. APHA denotes the Hazen color number according to DIN 53.409. (Deutsche Industrie Norm 53,409).

EXAMPLE 2

0.03 g of $\epsilon$-caprolactam is dissolved in 100 g of benzoyl chloride. The sample is stored in the dark. The sample is still colorless after storage for several months. An untreated sample of the same material had a color number of 150 APHA.

EXAMPLE 3

0.01 g of dicyclopentadiene is dissolved in 100 g of benzoyl chloride. The sample is still colorless after storage in the dark for several months. A comparison sample of the same material had a color number of 150 APHA.

EXAMPLE 4

0.02 g of acetophenone is dissolved in 100 g of o-toluic acid chloride. The sample is still colorless even after storage in the dark for several months. A comparison sample of the same material had a color number of 100 APHA.

EXAMPLE 5

0.05 g of triethyl phosphite is dissolved in 100 g of benzoyl chloride. The sample is still colorless after storage in the dark for several months. A comparison sample of the same material had a color number of 150 APHA.

EXAMPLE 6

0.05 g of ε-caprolactam is dissolved in 100 g of benzoyl chloride, with a color number of 200 APHA. The sample is colorless after 4 hours (APHA <15).

EXAMPLE 7

0.02 g of malonic acid diethyl ester is dissolved in 100 g of benzoyl chloride. The product is still colorless after storage in the dark for several months. A comparison sample of the same material had a color number of 150 APHA.

EXAMPLE 8

0.05 g of cyclohexene is dissolved in 100 g of benzoyl chloride, with a color number of 100 APHA. The sample is colorless after 2 hours (10 APHA).

Further examples, which are summarized in Tables 1-3, were carried out by a procedure corresponding to that given in Examples 1-8.

TABLE 1

| Example No. | Acid chloride | Stabilizer formula | Stabilizer name | amount (%) | Color number (APHA) with stabilizer | Color number (APHA) without stabilizer |
|---|---|---|---|---|---|---|
| 9 | Benzoyl chloride | II | Acetone | 0.05 | 5 | 150 |
|  |  | II | Acetophenone | 0.02 | 20 | 90 |
|  |  | II | Acetaldehyde | 0.01 | 10 | 80 |
|  |  | II | Benzaldehyde | 0.5 | 20 | 90 |
|  |  | II | Acrolein | 0.2 | 10 | 90 |
|  |  | II | ε-Caprolactam | 0.03 | 10 | 150 |
|  |  | II | Laurin lactam | 0.1 | 20 | 90 |
|  |  | II | Cyclohexanone | 0.1 | 10 | 150 |
| 10 | p-Chlorobebnzoyl chloride | II | Acetone | 0.2 | 20 | >100 |
|  |  | II | ε-Caprolactam | 0.2 | 20 | >100 |
| 11 | O-Toluic acid chloride | II | Acetone | 0.2 | 20 | >100 |
|  |  | II | ε-Caprolactam | 0.2 | 20 | >100 |
| 12 | Anisic acid chloride | II | Acetone | 0.2 | 20 | >100 |
|  |  | II | ε-Caprolactam | 0.2 | 20 | >100 |

TABLE 2

| Example No. | Acid chloride | Stabilizer formula | Stabilizer name | amount (%) | Color number (APHA) with stabilizer | Color number (APHA) without stabilizer |
|---|---|---|---|---|---|---|
| 13 | Benzoyl chloride | III | Cyclohexene | 0.05 | 10 | 100 |
|  |  | III | Allyl alcohol | 0.5 | 20 | 90 |
|  |  | III | Dicyclopentadiene | 0.01 | 10 | 150 |
|  |  | III | Undecenoic acid | 0.5 | 40 | 100 |
|  |  | III | Maleic acid | 0.5 | 10 | 90 |
|  |  | III | Fumaric acid | 0.5 | 10 | 90 |
|  |  | III | Acrylic acid methyl ester | 0.5 | 10 | 70 |
|  |  | III | Vinyl acetate | 0.5 | 20 | 90 |
|  |  | III | Cinnamic acid | 0.5 | 30 | 90 |
| 14 | m-Chloro-benzoyl chloride | III | Cyclohexene | 0.5 | 10 | 100 |
| 15 | O-Toluic acid chloride | III | Cyclohexene | 0.5 | 20 | >100 |
| 16 | Anisic acid chloride | III | Cyclohexene | 0.5 | 20 | >100 |

TABLE 3

| Example No. | Acid chloride | Stabilizer formula | Stabilizer name | amount (%) | Color number (APHA) with stabilizer | Color number (APHA) without stabilizer |
|---|---|---|---|---|---|---|
| 17 | Benzoyl chloride | IV | Triethyl phosphite | 0.3 | 10 | 100 |
| 18 | O-Toluic acid chloride | " | Triethyl phosphite | 0.3 | 20 | >100 |
| 19 | p-Chloro-benzoyl chloride | " | Triethyl phosphite | 0.3 | 20 | 100 |
| 20 | Anisic acid chloride | " | Triethyl phosphite | 0.3 | 20 | >100 |
| 21 | Benzoyl chloride | IV | Phosphorus trichloride | 0.2 | 10 | 150 |
| 22 | O-Toluic acid chloride | " | Phosphorus trichloride | 0.2 | 20 | >100 |
| 23 | p-Chloro-benzoyl | " | Phosphorus tri- | 0.2 | 10 | 100 |

TABLE 3-continued

| Example No. | Acid chloride | Stabilizer formula | name | amount (%) | Color number (APHA) with stabilizer | without stabilizer |
|---|---|---|---|---|---|---|
|  | chloride |  | chloride |  |  |  |
| 24 | Anisic acid chloride | " | Phosphorus trichloride | 0.2 | 20 | >100 |
| 25 | Benzoyl chloride | IV | Arsenic trichloride | 0.3 | 10 | 150 |

What is claimed is:

1. A process for color stabilizing an aromatic carboxylic acid chloride of the formula

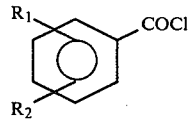

wherein

R₁ and R₂ independently represent hydrogen and halogen, alkyl or alkoxy which comprises introducing into a composition containing said aromatic carboxylic acid chloride 0.001 to 2% by weight of a color stabilizer, based upon the amount of said carboxylic acid chloride, said color stabilizer being selected from the group consisting of A. A stabilizer of the formula

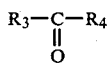

wherein

R₃ and R₄ can be identical or different and represent hydrogen, halogen, hydroxy, alkoxy, aryloxy, aralkoxy, alkyl, aralkyl, aryl, alkenyl or mono- or dialkylamino radicals;

R₃ and R₄ together with the carbonyl group can further form a ring;

B. A stabilizer of the formula

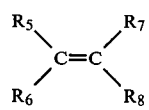

wherein

R₅ to R₈ are identical or different and represent hydrogen, nitrile, halogen, carboxyl, carbaryloxy, carbalkoxy, alkoxy, aryloxy, acyloxy, alkyl, aryl, aralkyl or alkenyl and R₅ and R₆ and/or R₇ and R₈, or R₅ and R₇, and/or R₆ and R₈ together with the atoms to which they are linked, can further form a ring; and C. A stabilizer of the formula

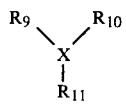

wherein

R₉ to R₁₁ can be identical or different and represent alkyl, aryl, alkoxy, or aralkoxy and X denotes phosphorus or arsenic.

2. A color stabilized aromatic acid chloride of the formula

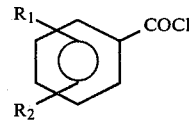

wherein

R₁ and R₂ independently represent hydrogen, halogen, alkyl or alkoxy containing 0.001 to 2% by weight of a color stabilizer selected from the group consisting of a compound of the formula

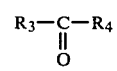

wherein

R₃ and R₄ can be identical or different and represent hydrogen, halogen, hydroxy, alkoxy, aryloxy, aralkoxy, alkyl, aralkyl, aryl, alkenyl or mono- or dialkylamino radicals;

R₃ and R₄ together with the carbonyl group can further form a ring of a compound of the formula

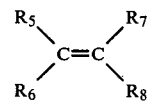

wherein

R₅ to R₈ are identical or different and represent hydrogen, nitrile, halogen, carboxyl, carbaryloxy, carbalkoxy, alkoxy, aryloxy, acyloxy, alkyl, aryl, aralkyl or alkenyl and R₅ and R₆ and/or R₇ and R₈, or R₅ and R₇, and/or R₆ and R₈ together with the atoms to which they are linked can further form a ring; and of a compound of the formula

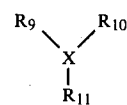

wherein

R₉ or R₁₁ can be identical or different and represent alkyl, aryl, alkoxy or aralkoxy; and X denotes phosphorus or arsenic.

3. A process according to claim 1 wherein the stabilizer is added in an amount of 0.01 to 0.5% by weight.

4. A process according to claim 1 wherein said stabilizer has the formula

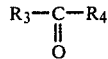

wherein $R_3$ and $R_4$ can be identical or different and represent hydrogen, halogen, hydroxy or optionally substituted alkoxy, aryloxy, aralkoxy, alkyl, aralkyl, aryl, alkenyl or mono- or di-alkylamino radicals, and $R_3$ and $R_4$ together with the carbonyl group can furthermore form an optionally substituted ring.

5. A process according to claim 1 wherein said stabilizer has the formula

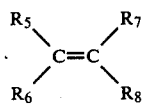

wherein $R_5$ to $R_8$ are identical or different and represent hydrogen, nitrile, halogen, carboxyl, optionally substituted carbalkoxy, carbaryloxy, alkoxy, aryloxy, acyloxy, alkyl, aryl, aralkyl or alkenyl radicals and $R_5$ and $R_6$, and/or $R_7$ and $R_8$, or $R_5$ and $R_7$, and/or $R_6$ and $R_8$, together with the atoms to which they are linked can furthermore form an optionally substituted ring.

6. A process according to claim 1 wherein said stabilizer has the formula

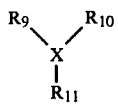

wherein $R_9$ to $R_{11}$ can be identical or different and represent optionally substituted alkyl, aryl, alkoxy or aralkoxy radicals and X denotes phosphorus or arsenic.

7. A process according to claim 1 wherein said stabilizer is acetone, ethyl acetoacetate, dicyclopentadiene, maleic acid, cyclohexanone, ε-caprolactam, phosphorus trichloride or triethyl phosphite.

8. A color stabilized aromatic carboxylic acid chloride according to claim 2 wherein said stabilizer is present in an amount of 0.01 to 0.5% by weight.

9. A color stabilized aromatic carboxylic acid chloride according to claim 2 wherein said stabilizer has the formula

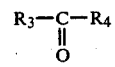

wherein $R_3$ and $R_4$ can be identical or different and represent hydrogen, halogen, hydroxy or optionally substituted alkoxy, aryloxy, aralkoxy, alkyl, aralkyl, aryl, alkenyl or mono- or di-alkylamino radicals, and $R_3$ and $R_4$ with the carbonyl group, can furthermore form an optionally substituted ring.

10. A color stabilized aromatic carboxylic acid chloride according to claim 2 wherein said stabilizer has the formula

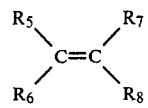

wherein $R_5$ to $R_8$ are identical or different and represent hydrogen, nitrile, halogen, carboxyl, optionally substituted carbalkoxy, carbaryloxy, alkoxy, aryloxy, acyloxy, alkyl, aryl, aralkyl or alkenyl radicals and $R_5$ and $R_6$, and/or $R_7$ and $R_8$, or $R_5$ and $R_7$, and/or $R_6$ and $R_8$, with the atoms to which they are linked can furthermore form an optionally substituted ring.

11. A color stabilized aromatic carboxylic acid chloride according to claim 2 wherein said stabilizer has the formula

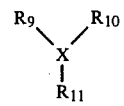

wherein $R_9$ to $R_{11}$ can be identical or different and represent optionally substituted alkyl, aryl, alkoxy or aralkoxy radicals and X denotes phosphorus or arsenic.

12. A process according to claim 4, wherein $R_3$ and $R_4$ which are identical or different represent hydrogen, halogen, hydroxy, alkoxy, aryloxy, aralkoxy alkyl, aralkyl, aryl, alkenyl or mono- or di-alkylamino; and $R_3$ and $R_4$ together with the carbonyl group can further form a ring.

13. A process according to claim 4, wherein $R_3$ and $R_4$ which are identical or different represent hydrogen, halogen, hydroxy, alkoxy, aralkoxy, alkyl, aralkyl, phenyl, toluyl, p-chlorophenyl, p-methoxyphenyl, alkenyl or mono- or di-alkylamino or $R_3$ and $R_4$ together with the carbonyl group can further form a ring.

14. A color stabilized aromatic carboxylic acid chloride according to claim 9, wherein $R_3$ and $R_4$ which are identical or different represent hydrogen, halogen, hydroxy, aryloxy, aralkoxy, alkoxy, alkyl, aryl, aralkyl, alkenyl or mono- or di-alkylamino and $R_3$ and $R_4$ together with the carbonyl group can further form a ring.

15. A color-stabilized aromatic carboxylic acid chloride according to claim 9, wherein $R_3$ and $R_4$ which are identical or different represent hydrogen, halogen, hydroxy, alkoxy, aralkoxy, alkyl, aralkyl, phenyl, toluyl, p-chlorophenyl, p-methoxyphenyl, alkenyl or mono- or di-alkylamino, or $R_3$ and $R_4$ together with the carbonyl group can further form a ring.

* * * * *